US009835583B2

(12) United States Patent
Han et al.

(10) Patent No.: US 9,835,583 B2
(45) Date of Patent: *Dec. 5, 2017

(54) REMOTE SENSING USING PULSE-WIDTH MODULATION

(71) Applicant: International Business Machines Corporation, Armonk, NY (US)

(72) Inventors: Shu-Jen Han, Cortlandt Manor, NY (US); Keith A. Jenkins, Sleepy Hollow, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 175 days.

This patent is subject to a terminal disclaimer.

(21) Appl. No.: 14/695,205

(22) Filed: Apr. 24, 2015

(65) Prior Publication Data
US 2016/0313275 A1 Oct. 27, 2016

(51) Int. Cl.
*G01N 27/00* (2006.01)
*G01N 27/414* (2006.01)
*G01N 33/00* (2006.01)

(52) U.S. Cl.
CPC ..... *G01N 27/4141* (2013.01); *G01N 33/0075* (2013.01); *G01N 27/4146* (2013.01)

(58) Field of Classification Search
CPC ............ G01N 27/4141; G01N 27/414; G01N 27/4143; G01N 27/4145; G01N 27/4146; G01N 27/4148
See application file for complete search history.

(56) References Cited

U.S. PATENT DOCUMENTS

| 7,686,929 | B2 | 3/2010 | Toumazou et al. |
| 2003/0001626 | A1* | 1/2003 | Kertis .............. G01R 19/16519 327/78 |
| 2004/0132070 | A1 | 7/2004 | Star et al. |
| 2007/0025048 | A1* | 2/2007 | Gokita ................. G01R 19/003 361/160 |
| 2008/0297957 | A1* | 12/2008 | Mehas .................... H02M 1/32 361/18 |

(Continued)

OTHER PUBLICATIONS

List of IBM Patents or Patent Applications Treated as Related; (Appendix P), Filed Jul. 9, 2015; 2 pages.

(Continued)

*Primary Examiner* — Blake A Tankersley
(74) *Attorney, Agent, or Firm* — Cantor Colburn LLP; Vazken Alexanian

(57) ABSTRACT

A method of assembling a remote sensor system to detect a gas or chemical and a remote sensor system are described. The method includes fabricating a sensor, the sensor outputting a sensor signal that changes upon contact of the sensor with the gas or chemical and the sensor having an input port for a clock signal, coupling a capacitor to the sensor, the capacitor output voltage resulting from the sensor signal output by the sensor, and coupling a mixer to the capacitor and a low frequency oscillator, the mixer configured to mix the capacitor output voltage with the low frequency oscillator output to generate an output signal. The method also includes coupling an antenna to the mixer, the antenna configured to transmit the output signal indicating detection of the gas or chemical.

8 Claims, 7 Drawing Sheets

(56) References Cited

U.S. PATENT DOCUMENTS

| | | | | |
|---|---|---|---|---|
| 2009/0195230 A1* | 8/2009 | Adkins | ............... | H02M 3/156 323/282 |
| 2012/0028820 A1* | 2/2012 | Rhodes | ............... | B82Y 15/00 506/9 |
| 2012/0256697 A1* | 10/2012 | Singerl | ............... | H03F 3/187 332/109 |
| 2012/0329193 A1 | 12/2012 | Guo et al. | | |
| 2013/0176563 A1 | 7/2013 | Ozawa et al. | | |
| 2014/0145148 A1 | 5/2014 | Lee | | |
| 2014/0336474 A1 | 11/2014 | Arbabian et al. | | |
| 2016/0097731 A1* | 4/2016 | Usagawa | ............... | G01N 27/12 73/31.06 |

OTHER PUBLICATIONS

Shu-Jen Han et al., "Remote Sensing Using Pulse-Width Modulation", U.S. Appl. No. 14/744,574, filed Jun. 19, 2015.

Chen et al., "Electronic Detection of Lectins Using Carbohydrate-Functionalized Nanostructures: Graphene versus Carbon Nanotubes," ACS Nano, vol. 6, No. 1, 2012, pp. 760-770, Jan. 24, 2013.

Do et al., "An improved inverter-based readout scheme for low-power ISFET sensing array", Electronics Letters, vol. 49, No. 24, 2013, pp. 1-2, Nov. 21, 2013.

Liu et al., "Minimal readout scheme for ISFET sensing arrays based on pulse width modulation", Electronics Letters, vol. 48, No. 10, 2012, pp. 1-2, May 10, 2012.

Ohno et al., "Label-Free Biosensors Based on Aptamer-Modified Graphene Field-Effect Transistors", Journal of the American Chemical Society, vol. 132, No. 51, 2010, pp. 18012-18013, Dec. 3, 2010.

* cited by examiner

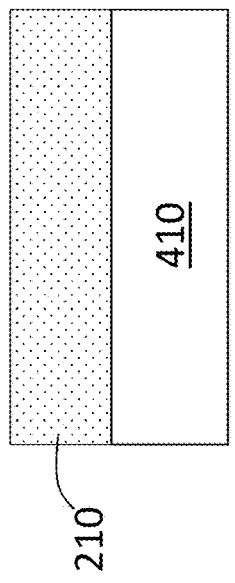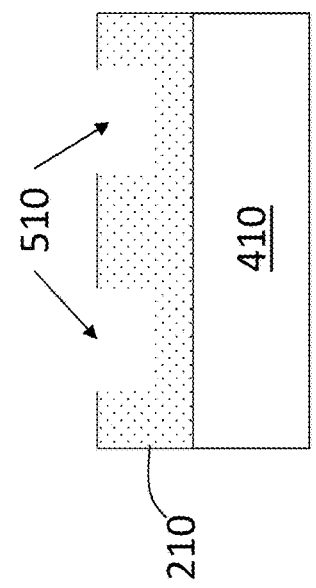

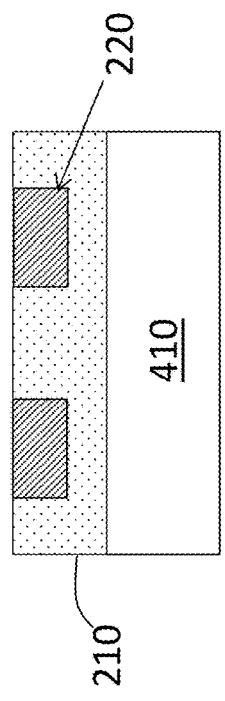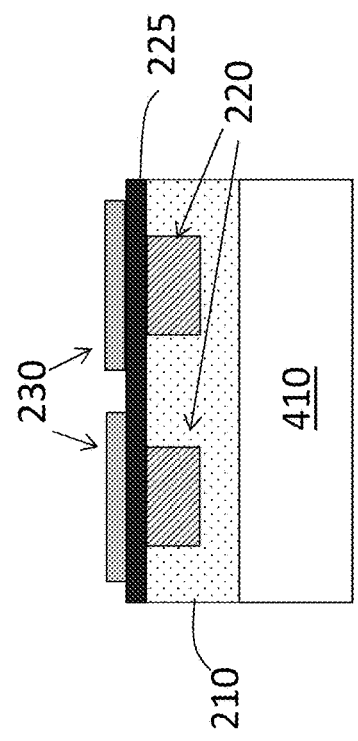

REMOTE SENSING USING PULSE-WIDTH MODULATION

BACKGROUND

The present invention relates to remote sensing, and more specifically, to remote sensing using pulse-width modulation.

Remote sensing involves a sensor providing information about conditions at a location without an operator having to be present at that location. Remote sensing facilitates environmental monitoring, for example, without requiring the presence of personnel. Generally, carbon nanotube, graphene, or other two-dimensional materials are used as sensors for environmental monitoring due to their large surface-to-volume ratio and good electronic properties. However, the wireless transmission of the information obtained with the sensors typically suffers from attenuation over longer distances.

SUMMARY

According to one embodiment of the present invention, a method of assembling a remote sensor system to detect a gas or chemical includes fabricating a sensor, the sensor outputting a sensor signal that changes upon contact of the sensor with the gas or chemical and the sensor having an input port for a clock signal; coupling a capacitor to the sensor, the capacitor output voltage resulting from the sensor signal output by the sensor; coupling a mixer to the capacitor and a low frequency oscillator, the mixer configured to mix the capacitor output voltage with the low frequency oscillator output to generate an output signal; and coupling an antenna to the mixer, the antenna configured to transmit the output signal indicating detection of the gas or chemical.

According to another embodiment, a remote sensor system includes a sensor configured to receive an input signal and output a sensor signal that changes upon the sensor contacting the gas or chemical; a capacitor coupled to the sensor, the capacitor configured to output an output voltage resulting from the sensor signal; and a mixer configured to mx the output voltage with a low frequency oscillator output to generate an output signal.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 4-9 are cross-sectional views illustrating some of the processes involved in fabricating the sensor according to an embodiment of the invention, in which:

FIG. 4 shows an oxide layer deposited on a complementary metal-oxide-semiconductor (CMOS) circuit;

FIG. 5 shows trenches formed in the oxide layer of the structure shown in FIG. 4;

FIG. 6 shows the gates formed in the oxide layer;

FIG. 7 shows the gate dielectric and channel material deposited over the gates;

FIG. 8 shows pFET metal deposited on the gate dielectric;

FIG. 9 shows nFET metal deposited on the gate dielectric; and

DETAILED DESCRIPTION

As noted above, remote sensors facilitate environmental monitoring and the detection of gas or chemicals (e.g., potentially harmful chemicals) without requiring the presence of any personnel. In existing remote sensor systems, the attenuation of transmitted sensor signals over long distances has affected the utility of remote sensing. For example, when sensor conductance changes due to the concentration of a gas, attenuation of the signal conveying that information affects the accuracy of the information received at a long distance from the sensor. Embodiments of the systems and methods detailed herein relate to a remote sensor system that changes duty cycle (performs pulse width modulation) in response to sensing gas or chemicals such that the sensor output signal may be transmitted long distances without attenuation issues affecting the reception of accurate sensor information.

Figure 1:
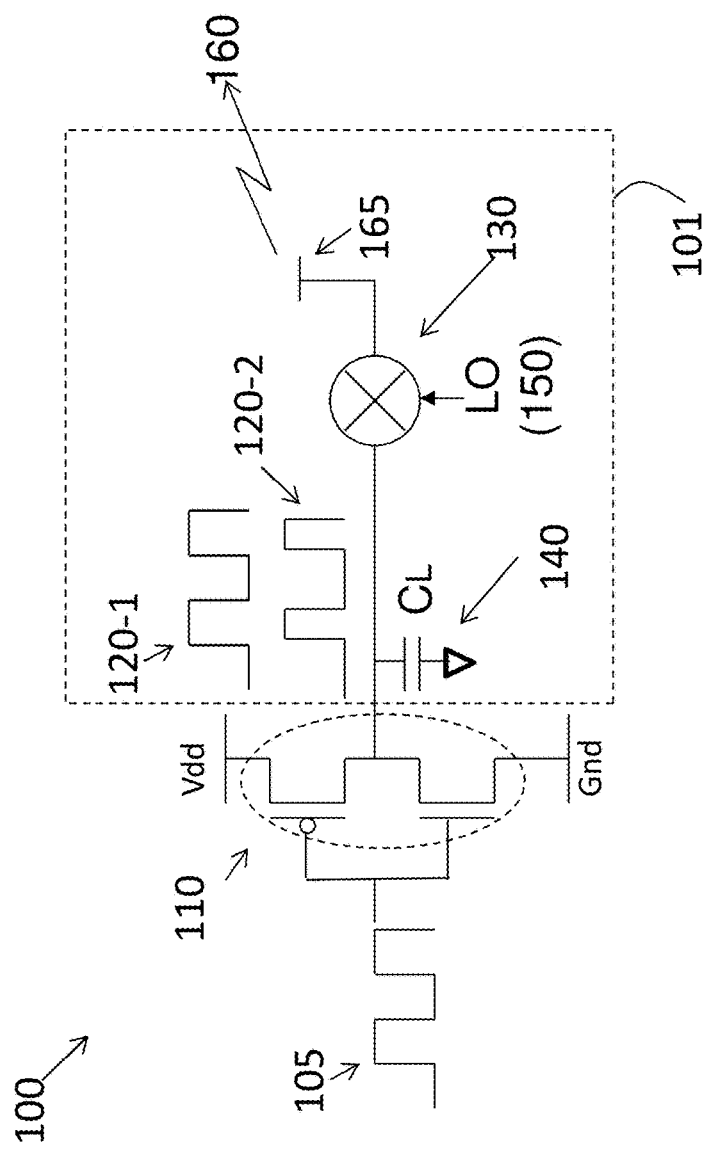
FIG. 1 shows a sensor system according to an embodiment of the invention.
Figure 2:
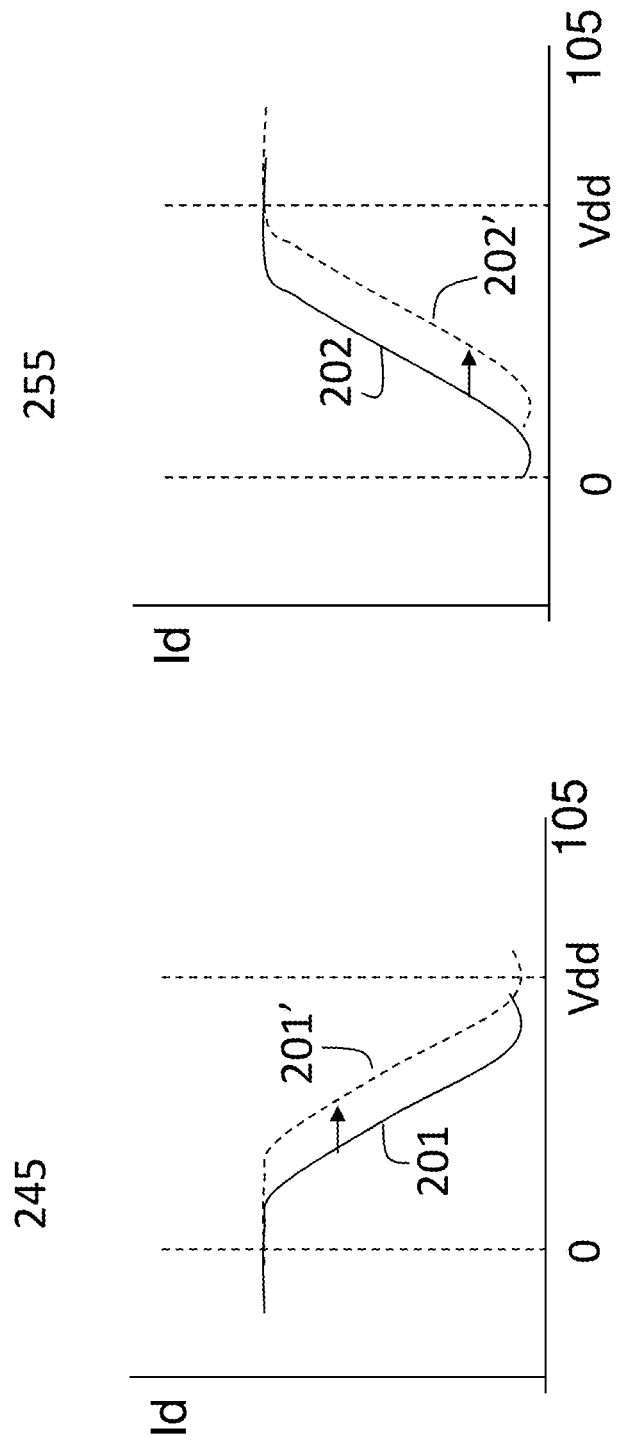
FIG. 2 illustrates a shift in the characteristic input signal to drain current Id curve the pFET and the nFET of the sensor system according to embodiments.

FIG. 1 shows a sensor system 100 according to an embodiment of the invention. The system 100 according to the embodiment detailed herein facilitates wireless transmission of information indicating a concentration of gas or a chemical in the environment in which the system 100 is located, and thus acts as a remote chemical detector. The system 100 includes a sensor 110. The sensor 110, detailed with reference to FIG. 2 below, includes an inverter having a p-channel field effect transistor (pFET) 245 (FIG. 2) and n-channel FET (nFET) 255 (FIG. 2). An output node of the sensor 110 charges and discharges a capacitor 140 based on an input signal 105 and any gas or chemical in the environment, as further discussed below. The input signal 105 may be provided by a known clock circuit that includes a ring oscillator or an LC-tank oscillator, for example. This input signal 105 duty cycle is assumed to be constant (such that any changes in duty cycle of the sensor 110 output may be attributed to gas or chemical exposure.). However, in alternate embodiments, a calibration or regulation of the input signal 105 may be additionally performed by known methods.

As explained in further detail below, gas or chemical exposure of the sensor 110 affects threshold voltages of the pFET 245 and nFET 255, which, in turn, affects the charging and discharging of the capacitor 140. This is because charges on absorbed molecules and chemicals can dope the channel materials through electrostatic doping or charge transfer. Because the same species are absorbed by both the pFET 245 and the nFET 255, the threshold voltage of the pFET 245 changes equally (but with an opposite polarity to) the threshold voltage of the nFET 255. The opposite polarity results from the characteristic input signal 105 (or input gate bias Vg) to drain current Id curve 201, 202 of each of the pFET 245 and the nFET 255, respectively, as shown in FIG. 2. The shift to the dashed curves 201', 202' indicated by the arrows for each of the pFET 245 and nFET 255, respectively, indicates an exemplary shift based on gas or chemical exposure. In an inverter circuit, such as that of the sensor 110, only one transistor is "on" or has high drain current Id at a given moment. When the input signal 105 (or Vg) swings from 0 to Vdd, the pFET 245 gets switched off, as indicated by the curve 201, and the nFET 255 gets switched on, as indicated by the curve 202. As noted above, when the pFET 245 is on, it charges the capacitor 140, and when the nFET 255 is on, it discharges the capacitor 140. Thus, a shift (e.g., from 201 to 201' and from 202 to 202') based on absorbed gas or chemicals affects the length of time that the pFET 245 and, conversely, the nFET 255 stay on, thereby affecting the charging/discharging of the capacitor 140 and, ultimately, the duty cycle of the output signal 160.

According to an embodiment, when the input signal is low, the pFET 245 is conductive and charges the capacitor 140, and when the input signal is high, the nFET 255 is conductive and discharges the capacitor 140. Based on the gas or chemical concentration, the threshold voltages of the pFET 245 and nFET 255 may change such that the pFET 245 is on longer and the nFET 255 is (proportionately) on for a shorter length of time. In this exemplary case, the capacitor 140 would be charged longer and the pulse width of the capacitor 140 output voltage 120 would be longer (see e.g., output voltage 120-1 in comparison to output voltage 120-2). Alternately, based on the gas or chemical concentration, the threshold voltages of the pFET 245 and the nFET 255 may change such that the nFET 255 is on longer and the pFET 245 is (proportionately) on for a shorter length of time. In this exemplary case, the capacitor 140 would be discharged longer and the pulse width of the capacitor 140 output voltage 120 would be shorter (see e.g., output voltage 120-2 in comparison to output voltage 120-1).

According to the arrangement of the sensor system 100 in the embodiment shown in FIG. 1, the effect of chemical exposure of the sensor 110 manifests as a change in duty cycle (or pulse width modulation) of the voltage of the capacitor 140 (output voltage 120). This, in turn, facilitates wireless transmission of the sensor 110 information. The capacitor 140 has an initial output voltage 120-1, which may have a duty cycle of 50%, for example. The chemical exposure of the sensor 110 may change the duty cycle to that shown for output voltage 120-2, for example. As noted above, this change from output voltage 120-1 to output voltage 120-2 indicates a shorter pulse width or less time that the pFET 245 is on relative to the nFET 255 based on the shift in threshold voltages (of equally but with opposite polarities) of the pFET 245 and nFET 255 because of the chemical. A mixer 130 is used to mix the output voltage 120 with a local oscillator 150 to generate the transmitted output signal 160 of the system 100. The output signal 160 is transmitted via an antenna 165. Upon receipt at a site remote from a location of the sensor 110, the duty cycle (pulse width) of the output signal 160 (the duty cycle of the output voltage 120 of the capacitor 140) indicates whether gas or chemical was detected and may provide an indication of a characteristic of the gas or chemical at the sensor 110. The characteristic may be a concentration such that the change in pulse width (duty cycle) of the output signal 160 is proportional to the concentration of the gas or chemical to which the sensor 110 is exposed. In the embodiment shown in FIG. 1, the components of the system 100 other than the sensor 110 (e.g., capacitor 140, low-frequency oscillator 150) may be part of a different circuit 101. According to an exemplary embodiment discussed below, the sensor 110 and the other components of the system 100 may be integrated.

Figure 3:
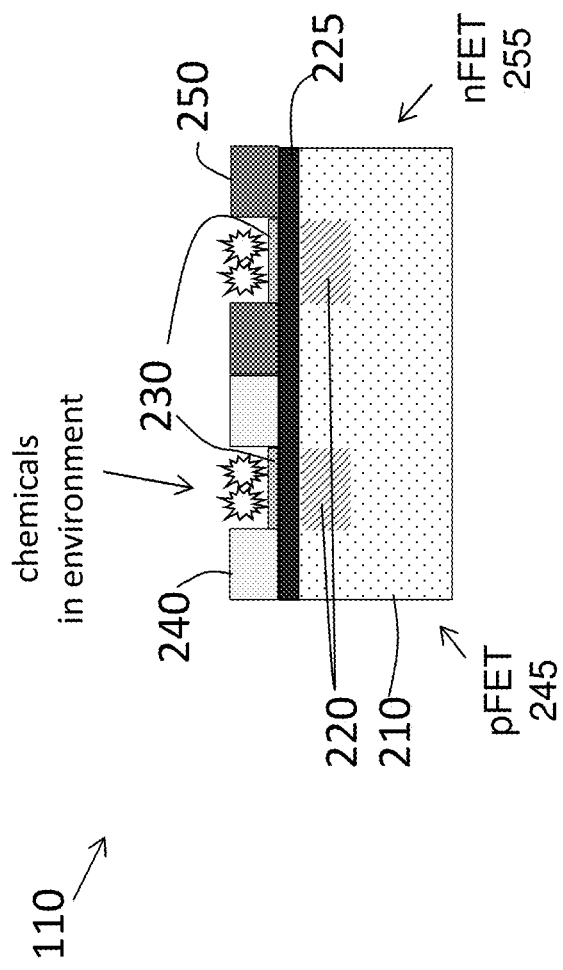
FIG. 3 details the sensor according to embodiments of the invention.

FIG. 3 details the sensor 110 according to embodiments of the invention. Some of the processes involved in fabricating the sensor 110 are detailed below. FIG. 2 details the components of the sensor 110 and specifically shows that the channel material 230 is exposed to the environment. As a result, the sensor 110 detects chemicals in the environment. The sensor 110 includes an oxide layer 210 with a gate 220 formed therein. Although the orientation shown in FIG. 3 does not show an electrical connection between the gate 220 of the pFET 245 and the gate 220 of the nFET 255, the gates 220 are electrically connected and receive the same input signal 105. A gate dielectric 225 is formed over the gate 220 and oxide layer 210. The pFET 245 and nFET 255 are defined by deposition of pFET metal 240 and nFET metal 250. The drain terminals of the pFET 245 and nFET 255 are electrically connected. The channel material 230 formed above the gate 220 (on the gate dielectric 225) may be a carbon nanotube (CNT) or graphene ribbon. Graphene is essentially a very thin (two-dimensional) layer of pure carbon. Absorption of gas or chemicals in the environment onto the graphene results in doping of the pFET 245 and nFET 255. This, in turn, affects the threshold voltage (the minimum gate-to-source voltage differential needed to create a conducting path between the source and drain terminals) of the pFET 245 and nFET 255. Detecting the shift in threshold voltages equates to detecting the concentration of chemical to which the sensor 110 is exposed. According to the embodiment detailed with reference to FIG. 1, the shift in the threshold voltages is not only detected but also indicated remotely because the system 100 facilitates manifesting the shift in threshold voltages in a capacitor 140 and transmitting the capacitor 140 output voltage 120 wirelessly.

The gas or chemical exposure of the channel material 230 (e.g., graphene) changes the conductance of the sensor 110 by changing the threshold voltages of the pFET 245 and the nFET 255. This change in conductance is converted to pulse width modulation of the output voltage 120 of the capacitor 140 of the system 100, as discussed above. Initially, with no chemical exposure, the pFET 245 may charge the capacitor 140 and the nFET 255 may discharge the capacitor 140 equally in the ideal case. In alternate embodiments, because the duty cycle of the output voltage 140 (the output signal 160) may not necessarily be 50% with no gas or chemical exposure, a calibration may be performed. That is, the duty cycle of the output signal 160 without any gas or chemical exposure of the sensor 110 may be used as a baseline (in a calibration process) to determine the change in duty cycle following gas or chemical exposure rather than assuming a duty cycle of 50% as a default. Alternatively, a reference sensor may be encapsulated such that its electrical properties do not change based on chemical exposure. A comparison of the transmitted output signal 160 to the signal output by the reference sensor may be used in lieu of a calibration to address any uncertainty in the clock input signal 105.

Figure 8:
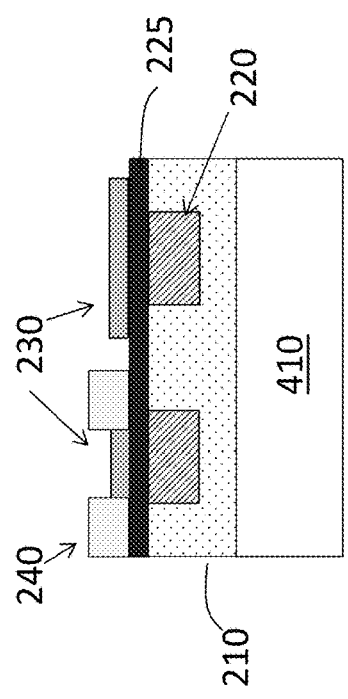
Figure 9:
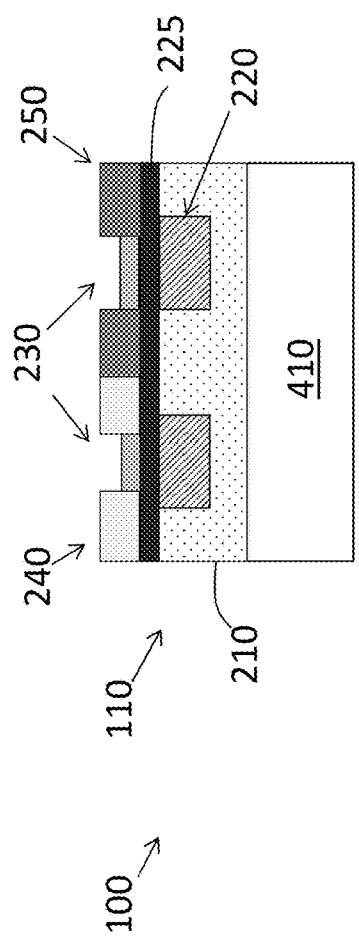

FIGS. 4-9 are cross-sectional views illustrating some of the processes involved in fabricating the sensor 110 according to an embodiment of the invention. FIG. 4 shows an oxide layer 210 deposited on a complementary metal-oxide-semiconductor (CMOS) circuit 410. In alternate embodiments, the oxide layer 210 may be deposited on a substrate. When the sensor 110 is formed on a CMOS circuit 410 that includes the capacitor 140 and transmission components, a separate circuit including those components need not be coupled to the sensor 110. Lithography and a reactive ion etch (RIE) process are used to form trenches 510 in the oxide layer 210, as shown in FIG. 5. As shown in FIG. 6, a gate metal deposition is performed followed by chemical mechanical planarization to form the embedded gate 220. FIG. 7 shows the result of completing two processes. A gate dielectric 225 is deposited by atomic layer deposition (ALD) or chemical vapor deposition (CVD). The gate dielectric 225 may be comprised of hafnium oxide ($HfO_2$), silicon dioxide ($SiO_2$), or aluminum oxide ($Al_2O_3$), for example. This deposition is followed by deposition and patterning of the channel material 230. As noted above, the channel material 230 may be comprised of carbon nanotube (CNT), graphene, or another two-dimensional semiconductor. In FIG. 8, the result of depositing and patterning a pFET metal 240 is shown. The pFET metal 240 may be a high workfunction metal such as palladium (Pd), nickel (Ni), or chromium (Cr), for example. FIG. 8 shows the result of depositing and patterning an nFET metal 250. The nFET metal 250 may be a low workfunction metal such as scandium (Sc) or erbium (Er), for example. At this stage, the sensor 110 may be connected to the CMOS circuit 410 to form the sensor system 100. In alternate embodiments, the sensor 110, formed on a substrate, may be connected to the other components of the system 100.

Figure 10:
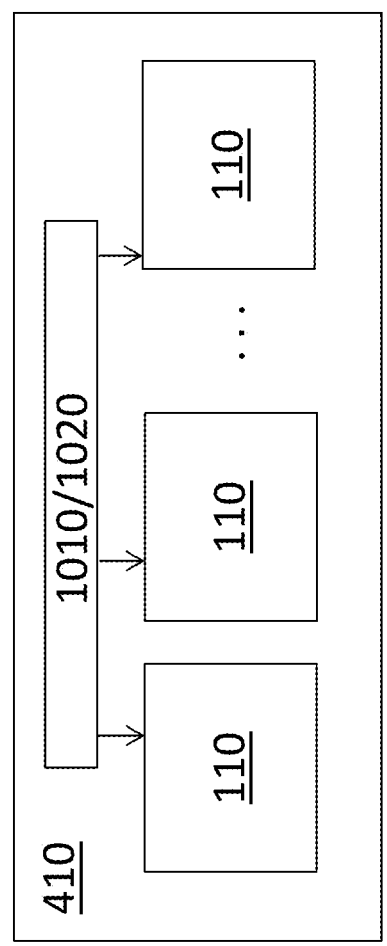
FIG. 10 shows an array of the sensors according to embodiments.

FIG. 10 shows an array of the sensors 110 according to embodiments discussed herein. Two or more sensors 110 may be arranged in an array on the CMOS circuit 410, for example, with each sensor 110 of the array designed to be sensitive to a different variety of chemicals. A selector 1010 may determine which of the sensors 110 transmits the output signal 160. Power consumption of the array of sensors 110 may be controlled by using a timing circuit 1020 that activates and de-activates each sensor 110, clock input (that provides the input signal 105), and transmission circuit as needed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of assembling a remote sensor system in an environment to detect a gas or chemical, the method comprising:
    fabricating a sensor, the sensor outputting a sensor signal that changes upon contact of the sensor with the gas or chemical and the sensor having an input port for a clock signal, wherein the fabricating the sensor includes forming a p-channel field effect transistor (pFET) and n-channel field effect transistor (nFET) and fabricating the sensor to change a threshold voltage of the pFET and a threshold voltage of the nFET based on the sensor contacting the gas or chemical;
    coupling a capacitor to the sensor, the capacitor output voltage resulting from charging or discharging of the capacitor according to the sensor signal output by the sensor;
    coupling a mixer to the capacitor and a low frequency oscillator, the mixer configured to mix the capacitor output voltage with the low frequency oscillator output to generate an output signal; and
    coupling an antenna to the mixer, the antenna configured to transmit the output signal indicating detection of the gas or chemical.

2. The method according to claim 1, wherein the capacitor output voltage being based on the threshold voltage of the pFET and the threshold voltage of the nFET includes a pulse width of the capacitor output voltage being based on the threshold voltage of the pFET and the threshold voltage of the nFET.

3. The method according to claim 1, wherein the fabricating the sensor includes fabricating the sensor to output a sensor signal that changes based on a concentration of the gas or chemical.

4. The method according to claim 1, wherein the fabricating the sensor includes disposing a channel material to be exposed to the environment.

5. The method according to claim 4, wherein the disposing the channel material includes disposing a two-dimensional semiconductor material.

6. The method according to claim 5, wherein the disposing the two-dimensional semiconductor material includes disposing carbon nanotube (CNT) or graphene.

7. The method according to claim 1, further comprising fabricating a plurality of the sensors in an array, each of the plurality of the sensors being configured to output an associated sensor signal that changes based on a different chemical.

8. The method according to claim 7, further comprising arranging a selector to select one of the plurality of the sensors to transmit the output signal.

* * * * *